United States Patent [19]

Ruddock

[11] 4,123,497
[45] Oct. 31, 1978

[54] PURIFICATION OF TECHNETIUM-99M PERTECHNETATE SOLUTIONS

[75] Inventor: Clinton F. Ruddock, Amersham, England

[73] Assignee: The Radiochemical Centre Limited, England

[21] Appl. No.: 661,552

[22] Filed: Feb. 25, 1976

[30] Foreign Application Priority Data

Mar. 6, 1975 [GB] United Kingdom ............... 9479/75

[51] Int. Cl.² ............................................. C01G 57/00
[52] U.S. Cl. ........................................ 423/2; 423/49; 424/1
[58] Field of Search ............. 423/2, 49; 252/301.1 R; 424/1

[56] References Cited

U.S. PATENT DOCUMENTS

| 3,745,119 | 7/1973 | Arino et al. | 252/301.1 R |
| 3,774,036 | 11/1973 | Gerhart | 252/301.1 R |
| 3,799,883 | 3/1974 | Arino et al. | 423/2 |
| 3,902,849 | 9/1975 | Barak et al. | 424/1 |

Primary Examiner—Edward A. Miller
Attorney, Agent, or Firm—Wenderoth, Lind & Ponack

[57] ABSTRACT

The invention provides a method and apparatus for preparing aqueous solutions of technetium-99m pertechnetate. In a preferred embodiment, the eluate from a technetium-99m generator is contacted with a cation-exchange resin having adsorbed thereon a cation which forms an insoluble salt with the anion of the generator eluate, whereby there is obtained an aqueous solution of the pertechnetate in water. The solution may be concentrated by adsorption of the pertechnetate on alumina, followed by desorption using a smaller volume of aqueous electrolyte.

9 Claims, 1 Drawing Figure

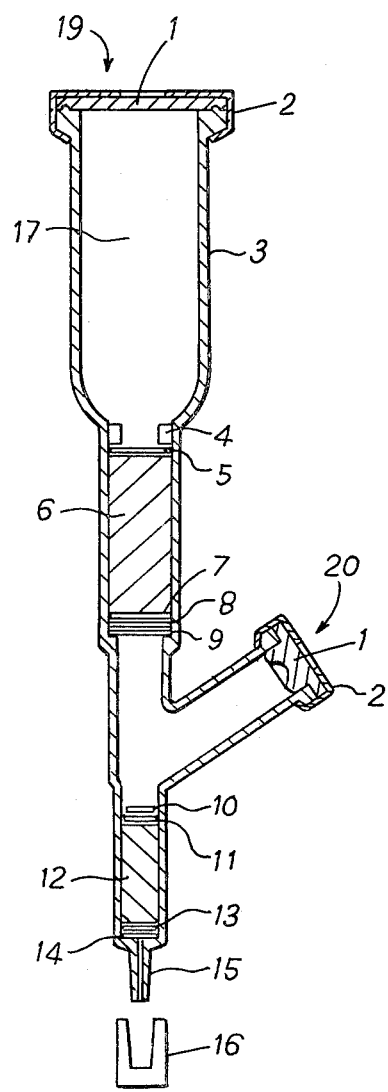

PURIFICATION OF TECHNETIUM-99M PERTECHNETATE SOLUTIONS

Technetium-99m generators comprise molybdenum-99 carried on a column of, for example, alumina. Technetium-99m is continuously generated on the column by radioactive decay, and can be eluted using aqueous saline solution as pertechnetate ion $TcO_4^-$. Such generators have a lifetime of about a week (the half lives of molybdenum-99 and technetium-99m are respectively 67 hours and 6 hours) and are very widely used.

Molybdenum-99 is conventionally made by irradiating either natural molybdenum, or molybdenum enriched in molybdenum-98, with neutrons in a reactor. Generators using molybdenum-99 produced by irradiation of molybdenum can have an activity of up to 500mCi and can be eluted once a day to provide solutions of technetium-99m at a radioactive concentration of up to 50mCi/ml but this may decrease to less than 5mCi/ml during the life of the generator. There are some uses for which this concentration is not high enough; an example is for bolus injections for dynamic studies where a concentration of 20mCi/ml is commonly required. There has been for 3 or 4 years a widespread need for solutions of technetium-99m at higher concentrations than can be obtained in the eluant of a conventional generator, and this need has been growing more acute with time. Many attempts have been made to fulfil this need, notably the following:-

(A) Molybdenum-99 produced by irradiation of molybdenum has been replaced by fission product molybdenum-99, which has an enormously higher specific activity and can be used in much smaller generators. But separated fission products are very expensive, and environmentally undesirable, in that their production gives rise to large quantities of highly radioactive by-product waste.

(B) Technetium-99m has been solvent extracted from reactor molybdenum-99, and the organic solvent removed by evaporation to leave the technetium-99m as a solid or concentrated aqueous solution. This procedure is too complex to be practised except in the largest hospitals.

(C) Pertechnetate ion in the eluate from conventional generators has been reduced by ferrous iron, co-precipitated with ferrous hydroxide, and re-dissolved in acid containing a chelating agent. Such a procedure is excessively complex and time-consuming, bearing in mind that the half life of the technetium-99m is only 6 hours. It also yields the technetium-99m in the form of a strong complex which is undesirable for certain applications.

(D) U.S. Pat. No. 3749556 describes a technique in which the eluate from a conventional generator is passed through a bed of powdered iron which reduces the pertechnetate ion and absorbs it while the remainder of the eluate is removed. The absorbed technetium-99m is then recovered by elution with a complexing agent therefor, such as an organic acid. A disadvantage of the technique is that the technetium-99m is recovered in reduced form and as a complex which may be inappropriate for its intended use.

The variety of these attempts indicates the magnitude of the problem.

It is an object of this invention to provide a practical technique for preparing a solution of pertechnetate ion in water.

It is a further object of this invention to provide a simple and practical technique for preparing a concentrated aqueous solution of pertechnetate ion.

In its broadest aspects, the present invention provides a method of preparing a solution of pertechnetate ion in water, which method comprises the steps of:

(1) Providing an aqueous electrolyte containing cations and anions and containing technetium-99m in the form of pertechnetate ion $TcO_4^-$;

(2) contacting the electrolyte with a material which removes anions other than pertechnetate from the solution by forming a water-insoluble compound therewith;

(3) if the electrolyte contains cations other than hydrogen, treating it with a cation-exchange resin, the treatment of step (3) being performed before or after or together with the treatment of step (2);

(4) and recovering a solution of pertechnetate ion in water.

The aqueous electrolyte containing pertechnetate ion may conveniently be provided in step (1) by passing an aqueous eluant containing cations and anions through a technetium-99 generator.

Technetium-99m generators are conventionally eluted with aqueous sodium chloride solution, although other eluants may be used provided that they do not displace molybdenum from the generator column. With a suitable choice of generator column, the anion may conveniently be halide, nitrate, sulphate, phosphate or an organic anion. The cation may conveniently be an alkali metal, ammonium or hydrogen, providing only that the eluant does not attack or corrode the column or the adsorbent material. The use of eluants other than sodium chloride solution may have positive advantages; for example, a generator carrying molybdenum-99 in the form of phosphomolybdate (which contains a higher proportion of molybdenum than does the conventional molybdate) may be elutable by sodium phosphate solution but not by sodium chloride solution.

According to one embodiment of the invention, when the anion of the generator eluant is chloride, bromide, a iodide or phosphate, the material used in step 2 may be silver oxide. This reacts with the eluate, precipitating an insoluble silver salt (halide or phosphate) and leaving pertechnetate in aqueous solution. In this embodiment, the eluate may be contacted either before or after contact with the silver oxide, with a bed of a cation-exchange resin in the hydrogen form; this step will normally be necessary to remove cations from the eluate unless the eluant used was acidic.

Alternatively, and this alternative is the preferred form of the invention, the electrolyte is contacted in step (2) and (3) combined, with a cation-exchange resin having adsorbed thereon a cation which forms an insoluble salt with the anion in the said aqueous eluant, whereby there is obtained an aqueous solution of the pertechnetate which is otherwise substantially free of cations and anions. We prefer to use strong cation-exchange resins such as that sold by Bio-Rad Laboratories under the trade mark Bio-Rad AG50 W-X12 (described as a strongly acidic cation exchange resin composed of nuclear sulphonic acid exchange groups attached to a styrene-divinylbenzene polymer lattice); and that sold by Zerolit Co. Ltd., under the Trade Mark Zerolit 225-SRC 16 (styrene-divinylbenzene polymer lattice). However we believe that weak cation-exchange resins and even inorganic cation adsorbents such as zirconium phosphate and ammonium phosphomolybate and natural and synthetic zeolites will be effective for this purpose.

The cation exchange resin carries an adsorbed cation which forms an insoluble salt with anions (other than pertechnetate) in the aqueous electrolyte. Thus, for example, when the anion in the electrolyte is chloride, bromide or iodide, the adsorbed cation may conveniently be silver; when the anion in the electrolyte is sulphate or phosphate, the adsorbed cation may conveniently be calcium, strontium or barium. When an eluant containing, for example, sodium and chloride ions in addition to pertechnetate, is contacted with a cation-exchange resin in the silver form, it is believed that silver chloride precipitates quantitatively, the cation-exchange resin is converted, at least in part, to the sodium form, and the remaining liquid is substantially free of ionic species other than pertechnetate. The adsorbed cation should preferably be one whose pertechnetate salt is water soluble; for example, silver pertechnetate has an appreciable solubility product. Most pertechnetates, other than those of tetraphenyl arsonium and caesuim are believed to be water soluble.

The desalination of sea water, by contact with a zeolite which had previously been treated with silver nitrate, has long been known, and was indeed put to practical use in marine survival kit in World War II. However, application of the technique to the recovery of radioactive materials is believed to be novel.

It is possible to contact the electrolyte with the cation exchange resin by passing the electrolyte through a packed column of the resin. However, the silver chloride (or other) precipitate tends to clog the system and coat the resin beads, so that high pressure may be needed to force all the liquid through the column, and there may be poor contact between the eluate and the resin. These difficulties are not insuperable, but may be avoided by providing the resin in loose form so that it is slurried with the electrolyte by using resin of small bead size, so as to present a large surface area: volume ratio to the adsorbing silver cation; and by using an excess of the resin. We prefer to use a cation-exchange resin which has been treated to saturation with silver nitrate or other salt, and to use at least a two-fold and preferably a three-fold, excess of resin over that stoichiometrically required for reaction with the sodium and chloride (or other ions) in the electrolyte.

For example, 15ml of isotonic (0.152M) saline contains 2.31mEq of sodium chloride. 2.31mEq of silver can be adsorbed from silver nitrate by about 1ml of Zerolit 225 SRC-16. We prefer to contact a 15ml isotonic saline generator eluate with at least 2ml, and optimally about 3ml, of the cation-exchange resin in the silver form.

According to a preferred form of the invention, briefly noted above, the resulting aqueous solution of pertechnetate may be concentrated by the steps of:

(5) contacting the said aqueous solution with a material to releasably adsorb the pertechnetate therefrom, and (6) contacting the material carrying the pertechnetate with a desired volume of an aqueous electrolyte and thereby recovering a solution of pertechnetate of desired concentration.

In step (5), the desalinated liquid is contacted with a material which releasably adsorbs the pertechnetate ion therefrom. We prefer to use as this material alumina, either a neutral grade or an acidic grade, although other inorganic anion exchangers such as zirconium dioxide and manganese dioxide may be used. The use of organic anion exchange resins is possible, provided that they do not adhere so tenaciously to the pertechnetate that it cannot afterwards be recovered. The alumina or other material is most conveniently provided in the form of a fixed bed through which the liquid is passed.

The weight of pertechnetate involved is so small that the volume of alumina or other material is really not critical. Provided that there is adequate contact between the liquid and the material, 0.25 ml of the latter is quite sufficient to quantitatively adsorb the pertechnetate.

While it has long been known that pertechnetate cannot be eluted from alumina by means of water, so that it has been conventional to use saline solution, it is believed novel to adsorb pertechnetate quantitatively on to alumina from solution in water.

In step (6), the pertechnetate is recovered in solution by contacting the material carrying the pertechnetate with a desired volume of an aqueous electrolyte. As in step (1) (conventional elution of technetium-99m generator), the nature of the electrolyte is not important provided that it is capable of displacing pertechnetate. If the resulting solution is to be used for injection, it will be convenient to use isotonic sodium chloride solution. The volume of aqueous electrolyte used, of course, controls the concentration factor achieved by the method. We have achieved concentration factors of up to 15, and expect to be able to do better than this. Thus, if the original technetium generator eluate had a volume of 15ml, and 1ml of isotonic saline solution was used to recover the pertechnetate from the alumina or other material in step (4), the concentration factor would be slightly less than 15, for example from 13 to 15, taking account of processing losses.

Performance may be improved if, in step (2) the cation-exchange resin is washed, after being contacted with the generator eluate, so as to ensure complete removal of the pertechnetate. When the eluate passes direct from the generator into contact with the cation-exchange resin, this may conveniently be achieved by using a larger volume of eluant than normal, e.g. 20 ml instead of 15ml; the last 5ml of eluant do not in fact elute any more pertechnetate but provide the required washing liquid.

In another aspect the present invention provides a column for preparing a concentrated solution of pertechnetate which column comprises:

a tubular shell; a first liquid inlet at one end of said shell;

a 1st and a 2nd porous disc enclosing a first zone within said shell adjacent to said first inlet;

within said first zone a cation-exchange resin having adsorbed thereon a cation which forms an insoluble salt with the anions in the aqueous eluant of a technetium-99m generator;

a liquid outlet at other end of said shell;

a 3rd and 4th porous disc enclosing a second zone within said shell intermediate said first zone and said liquid outlet;

within said second zone a material to releasably adsorb pertechnetate ion from an aqueous solution thereof;

and a second liquid inlet for introducing eluant only to said second zone.

Preferably the column is maintained in a sterile state and the liquid inlets and outlet comprise sterile coupling means such as pierceable autoclavable closures (PAC) or Luer closures.

This invention is expected to be of particular value for concentration of large volumes of Tc-99m pertechnetate for a separated Tc-99m distribution service. Such distribution services commonly utilise the complex solvent extraction process or an equally complex high temperature distillation process whereas this invention would permit concentration of large volumes of dilute pertechnetate obtained by simple elution of high activity generators. For example, a daily distribution service of about 4 Ci/day Tc-99m, at a reference time 18 hours after separation from the parent molybdenum-99, could be based on a conventional alumina adsorbent generator loaded with 150 Ci of Mo-99 and eluted daily for a week. The Mo-99 used could have a relatively low specific activity of about 1 Ci/gm and the pertechnetate could be eluted with about 10 liters of 0.1N hydrochloric acid. Concentration of the eluate by a factor of 25 to provide 400ml of pertechnetate solution at a radioactive concentration of 10 mCi/ml, at a reference time 18 hours after separation from the parent molybdenum-99, could be achieved by the method herein described.

Accordingly the invention contemplates the use of generators containing from 10mCi up to 1000 Ci or more of molybdenum-99 at a concentration of at least 0.1 Ci/gm; the concentration of eluates having a starting volume of from 5 ml up to 100 liters or even more; said concentration being by a factor of from 1.1 to 100 or more.

In the accompanying drawing, FIG. 1 is an axial cross section through a device according to the present invention. The column comprises:- a tubular shell 3, of injection moulded plastics material;

a first liquid inlet 19, at one end of said shell, comprising a PAC 1 and an aluminium overseal 2;

a resin bed top support 5, in the form of a porous disc retained by a retaining clip 4; a filter disc 7, surmounting a filter disc support 8, and a non-return valve 9; the resin bed top support 5, and filter disc 7, enclosing a first zone within the shell 3, adjacent first liquid inlet 19;

within said first zone a cation exchange resin 6, in the silver form;

a liquid outlet at the other end of said shell 3, comprising a Luer tip 15 and associated Luer closure 16;

an alumina top support 11, retained by a retaining disc 10; a filter retaining disc 13, surmounting a filter disc 14; the alumina bed top support 11, and the filter retaining disc 13, constituting third and fourth porous discs enclosing a second zone within the shell 3, intermediate the first zone and the liquid outlet;

within said second zone, alumina 12; and a second liquid inlet 20, for introducing eluant only to said second zone, comprising a PAC 1 and an associated aluminium overseal 2.

The device is operated by eluting a conventional technetium-99m generator, using isotonic saline as the eluant, directly into a reservoir 17, within the shell 3, above the cation-exchange resin 6. The eluate is then passed through both the resin 6, and the alumina 12, and into a container for waste through a needle attached to the Luer tip 15. The driving force for this operation can be either air-pressure applied at the top of the device for partial vacuum in the collection vial. The pertechnetate is recovered by injection of a small volume of isotonic saline through the second liquid inlet 20, on the side arm, and collection of the concentrated pertechnetate in a second sterile vial attached to a needle on the Luer tip 15.

This device may be modified to permit multiple use simply by increasing the size of the cation-exchange resin 6. Multiple use of such a device can give rise to the problem of clogging of the resin bed 6, by the silver chloride, or other water-insoluble material which is precipitated therein; but this problem can normally be overcome by the application of pressure e.g. 20 to 30 PSIG at the liquid inlet 19.

Thus a device intended for single use in association with a technetium-99m generator delivering 15ml of eluate might suitable contain from 2 to 5ml of the cation-exchange resin 6. A device intended for multiple e.g. 5-fold use in association with the same generator might contain from 5 to 20 mls of the cation-exchange resin 6. The use of more than about 20mls of resin may give rise to washing difficulties and is not preferred.

The solution of technetium-99m pertechnetate in water which is produced according to the present invention in its broadest form, is valuable and may have specific advantages over normal saline pertechnetate solutions in certain scanning applications. The invention, as applied to the production of concentrated solution of technetium-99m has the following advantages:-

(i) it prolongs the useful life of the generator (ii) the concentrate can be used for bolus injections (iii) it enables a generator to be eluated only 4–5 hours after the last elution, instead of 24 hours as is usual. In this connection, the technetium-99m activity (expressed as a percentage of the molybdenum activity at the time of elution) has only grown to about 30% after 4 hours, whereas it reaches 86% after 24 hours.

(iv) it is usual to obtain the eluate from a technetium-99m generator in a sterile form in which it can be directly injected. The concentration method of the present invention can readily be performed without loss of sterility.

(v) the technetium-99m in the eluate concentrate is present as pertechnetate in saline solution.

(vi) it can be operated at a very high concentration factor of 15 or more.

(vii) it provides technetium-99m solutions of improved radionuclidic purity, because impurities such as caesium-134 silver-110m and iodine 131 will be removed by the cation-exchange resin.

(viii) it results in lower molybdenum-99 contamination, since any breakthrough from the generator is either permanently adsorbed by the alumina or goes to waste in the discarded eluate.

(ix) additive contaminants in generator eluates do not remain in the final aqueous concentrate.

(x) the generator can be used to produce either normal or concentrated eluates at will.

The following examples illustrate the invention.

EXAMPLE 1

The eluate from a technetium-99m generator (15ml) was passed through a fixed bed of 3ml of Zerolit 225-SRCl 6 cation-exchange resin which had previously been washed with silver nitrate solution until saturated; and then through a fixed bed of 0.5ml of CAMAG acid washed alumina. This was followed by 2ml of wash water. The pertechnetate was eluted from the bed of alumina with 1ml of isotonic saline solution under gravity flow conditions. The yield was 95% giving a concentration factor of 14.25.

EXAMPLE 2

The eluate from a technetium-99m generator (20 ml i.e. 15ml + 5ml wash-liquid) was passed through a fixed bed of 4.5ml of Bio-Rad AG50W-X12 cation-exchange resin which had previously been washed with silver nitrate solution until satured; and then through a fixed bed of 0.25ml of WOELM acid grade W200 alumina. The pertechnetate was eluted from the bed of alumina with 3ml of isotonic saline solution under pressure. The yield was 98.5% giving a concentration factor of 6.57.

We claim:

1. A method of preparing a solution of pertechnetate ion in water, which method comprises the steps of:
   (1) providing an aqueous electrolyte containing cations and anions and containing technetium-99m in the form of pertechnetate ion $TcO_4^-$; and
   (2) contacting the electrolyte with a cation-exchange material having adsorbed on cation-exchange sites thereof a cation which forms an insoluble salt with said anions in said aqueous electrolyte, whereby there is obtained an aqueous solution of the pertechnetate which is otherwise substantially free of cations and anions.

2. A method as claimed in claim 1 wherein the aqueous electrolyte is obtained in step (1) by passing an aqueous eluant containing cations and anions through a technetium-99m generator.

3. A method as claimed in claim 2, wherein the generator eluant is aqueous saline solution.

4. A method as claimed in claim 1, wherein the cation-exchange material is a cation-exchange resin.

5. A method as claimed in claim 1, wherein the cation adsorbed on the cation-exchange material is $Ag^+$.

6. A method as claimed in claim 1 wherein, in step (2) the cation-exchange material is washed, after being contacted with the aqueous electrolyte, so as to ensure the complete removal of the pertechnetate.

7. a method as claimed in claim 1 wherein, the resulting aqueous solution of pertechnetate is concentrated by the steps of:
   (3) contacting the said aqueous solution with a material to releasably adsorb the pertechnetate therefrom and
   (4) contacting the material carrying the pertechnetate with a desired volume of an aqueous electrolyte and thereby recovering a solution of pertechnetate of desired concentration.

8. A method as claimed in claim 7, wherein the material used in step (3) to releasably adsorb the pertechnetate is alumina.

9. A method as claimed in claim 7, wherein the aqueous electrolyte used in step (4) to recover the pertechnetate is isotonic silane solution.

* * * * *